(12) United States Patent
Napolitano et al.

(10) Patent No.: US 8,784,318 B1
(45) Date of Patent: Jul. 22, 2014

(54) ABERRATION CORRECTION USING CHANNEL DATA IN ULTRASOUND IMAGING SYSTEM

(75) Inventors: David J. Napolitano, Pleasanton, CA (US); Ching-Hua Chou, Mountain View, CA (US); Ting-Lan Ji, San Jose, CA (US); Brian Derek DeBusschere, Orinda, CA (US); Glen W. McLaughlin, San Carlos, CA (US); Larry Y. L. Mo, San Ramon, CA (US); Robert W. Steins, Santa Clara, CA (US)

(73) Assignee: Zonare Medical Systems, Inc., Mountain View, CA (US)

( * ) Notice: Subject to any disclaimer, the term of this patent is extended or adjusted under 35 U.S.C. 154(b) by 544 days.

(21) Appl. No.: 11/492,557

(22) Filed: Jul. 24, 2006

Related U.S. Application Data

(60) Provisional application No. 60/701,635, filed on Jul. 22, 2005.

(51) Int. Cl.
| | |
|---|---|
| *A61B 8/00* | (2006.01) |
| *G01S 7/52* | (2006.01) |
| *A61B 8/08* | (2006.01) |
| *G01N 29/44* | (2006.01) |
| *G06T 5/50* | (2006.01) |

(52) U.S. Cl.
CPC .............. *G01S 7/52049* (2013.01); *A61B 8/00* (2013.01); *A61B 8/5269* (2013.01); *A61B 8/58* (2013.01); *G01S 7/52085* (2013.01); *G01S 7/52095* (2013.01); *G01N 29/4463* (2013.01); *G06T 5/50* (2013.01); *G06T 2207/10132* (2013.01); *G06T 2207/20172* (2013.01); *G06T 2207/30004* (2013.01)
USPC ............................................ 600/443; 73/620

(58) Field of Classification Search
USPC ............................................ 600/443; 73/620
See application file for complete search history.

(56) References Cited

U.S. PATENT DOCUMENTS

| 4,265,126 A | 5/1981 | Papadofrangakis |
|---|---|---|
| 4,604,697 A | 8/1986 | Luthra |

(Continued)

FOREIGN PATENT DOCUMENTS

WO    WO 2008/051738 A2    5/2008

OTHER PUBLICATIONS

Anderson, M.E., et al., "The Impact of Sound Speed Errors on Medical Ultrasound Imaging", *J. Acous. Soc. of Am.*, Jun. 2000, pp. 3540-3548, vol. 107, No. 6.

(Continued)

*Primary Examiner* — Long V. Le
*Assistant Examiner* — Angela M Hoffa
(74) *Attorney, Agent, or Firm* — Kory D. Christensen; Stoel Rives LLP

(57) ABSTRACT

Embodiments of the present invention provide an ultrasound scanner equipped with an image data processing unit that can perform adaptive parameter optimization during image formation and processing. In one embodiment, an ultrasound system comprises a channel data memory to store channel data obtained by digitizing ultrasound image data produced by an image scan; an image data processor configured to process the stored channel data in the memory to reconstruct an ultrasound image for each of a plurality of trial values of at least one parameter to be optimized; and a parameter optimization unit configured to evaluate an image quality of the reconstructed ultrasound image for each trial value of the at least one parameter, and to determine the optimized value of the at least one parameter based on the evaluated image quality.

31 Claims, 9 Drawing Sheets

(56) References Cited

U.S. PATENT DOCUMENTS

| | | | |
|---|---|---|---|
| 4,852,576 A | 8/1989 | Inbar et al. | |
| 4,852,577 A | 8/1989 | Smith et al. | |
| 5,161,535 A | 11/1992 | Short | |
| 5,260,871 A | 11/1993 | Goldberg | |
| 5,269,289 A | 12/1993 | Takehana et al. | |
| 5,313,948 A | 5/1994 | Murashita et al. | |
| 5,357,962 A * | 10/1994 | Green | 600/443 |
| 5,357,965 A | 10/1994 | Hall et al. | |
| 5,365,929 A | 11/1994 | Peterson | |
| 5,409,010 A | 4/1995 | Beach et al. | |
| 5,415,173 A | 5/1995 | Miwa et al. | |
| 5,417,215 A * | 5/1995 | Evans et al. | 600/442 |
| 5,555,534 A | 9/1996 | Maslak | |
| 5,566,674 A | 10/1996 | Weng | |
| 5,579,768 A | 12/1996 | Klesenski | |
| 5,581,517 A | 12/1996 | Gee et al. | |
| 5,623,928 A | 4/1997 | Wright et al. | |
| 5,654,509 A | 8/1997 | Miele et al. | |
| 5,690,111 A | 11/1997 | Tsujino | |
| 5,720,289 A * | 2/1998 | Wright et al. | 600/443 |
| 5,776,063 A | 7/1998 | Dittrich et al. | |
| 5,782,766 A | 7/1998 | Weng et al. | |
| 5,799,111 A | 8/1998 | Guissin | |
| 5,857,973 A | 1/1999 | Ma et al. | |
| 5,871,019 A | 2/1999 | Belohlavek | |
| 5,935,074 A | 8/1999 | Mo et al. | |
| 5,954,653 A | 9/1999 | Hatfield et al. | |
| 5,984,870 A | 11/1999 | Giger et al. | |
| 6,016,285 A | 1/2000 | Wright et al. | |
| 6,036,643 A | 3/2000 | Criton et al. | |
| 6,068,598 A | 5/2000 | Pan et al. | |
| 6,069,593 A | 5/2000 | Lebby et al. | |
| 6,102,859 A | 8/2000 | Mo | |
| 6,110,119 A | 8/2000 | Hall | |
| 6,113,544 A | 9/2000 | Mo | |
| 6,120,446 A | 9/2000 | Ji et al. | |
| 6,142,943 A | 11/2000 | Mo et al. | |
| 6,162,176 A | 12/2000 | Washburn et al. | |
| 6,193,663 B1 | 2/2001 | Napolitano et al. | |
| 6,221,020 B1 | 4/2001 | Lysyansky et al. | |
| 6,263,094 B1 | 7/2001 | Rosich et al. | |
| 6,312,385 B1 | 11/2001 | Mo et al. | |
| 6,315,728 B1 | 11/2001 | Muzilla et al. | |
| 6,322,509 B1 | 11/2001 | Pan et al. | |
| 6,358,205 B1 | 3/2002 | Ustuner et al. | |
| 6,390,983 B1 | 5/2002 | Mo et al. | |
| 6,398,733 B1 | 6/2002 | Simopoulos et al. | |
| 6,423,003 B1 | 7/2002 | Ustuner et al. | |
| 6,434,262 B2 | 8/2002 | Wang | |
| 6,450,959 B1 | 9/2002 | Mo et al. | |
| 6,464,637 B1 | 10/2002 | Criton et al. | |
| 6,464,640 B1 | 10/2002 | Guracar et al. | |
| 6,464,641 B1 | 10/2002 | Pan et al. | |
| 6,468,218 B1 | 10/2002 | Chen et al. | |
| 6,491,636 B2 | 12/2002 | Chenal et al. | |
| 6,497,661 B1 | 12/2002 | Brock-Fisher | |
| 6,503,203 B1 | 1/2003 | Rafter et al. | |
| 6,512,854 B1 | 1/2003 | Mucci et al. | |
| 6,547,737 B2 | 4/2003 | Njemanze | |
| 6,577,967 B2 | 6/2003 | Mo et al. | |
| 6,679,847 B1 | 1/2004 | Robinson et al. | |
| 6,860,854 B2 | 3/2005 | Robinson et al. | |
| 6,926,671 B2 | 8/2005 | Azuma et al. | |
| 6,932,770 B2 | 8/2005 | Hastings et al. | |
| 6,980,419 B2 | 12/2005 | Smith et al. | |
| 7,022,075 B2 | 4/2006 | Grunwald et al. | |
| 7,627,386 B2 | 12/2009 | Mo et al. | |
| 2004/0179332 A1 | 9/2004 | Smith et al. | |
| 2006/0074320 A1 | 4/2006 | Yoo et al. | |
| 2006/0079778 A1 | 4/2006 | Mo et al. | |
| 2008/0146922 A1 | 6/2008 | Steins et al. | |
| 2010/0189329 A1 | 7/2010 | Mo et al. | |

OTHER PUBLICATIONS

Haun, Mark Alden, "New Approached to Aberration Correction in Medical Ultrasound Imaging", Ph.D. Thesis, University of Illinois at Urbana-Champaign, 2003.

Jellins, J. et al., "Velocity compensation in water-coupled breast echography", *Ultrasonics*, Sep. 1973, pp. 223-226.

Liu, D., et al., "Adaptive Ultrasonic Imaging Using SONOLINE Elegra 198 ", *2000 IEEE Ultrasonics Symposium*, 4 pages.

Nock, L., et al., "Phase aberration correction in medical ultrasound using speckle brightness as a quality factor", *J. Acous. Soc. Am.*, May 1989, vol. 85, No. 5, pp. 1819-1833.

U.S. Appl. No. 10/961,709, filed Oct. 7, 2004, Mo et al.

U.S. Appl. No. 11/492,471, filed Jul. 24, 2006, Napolitano et al.

U.S. Appl. No. 11/586,212, filed Oct. 24, 2006, Steins et al.

U.S. Appl. No. 12/340,578, filed Dec. 19, 2008, Mo et al.

U.S. Appl. No. 12/628,169, filed Nov. 30, 2009, Mo et al.

Freeman, S., "Retrospective Dynamic Transmit Focusing", Ultrasonic Imaging 17, (1995), pp. 173-196.

Gammelmark, K.L., et al. "Multi-Element Synthetic Transmit Aperture Imaging using Temporal Encoding", 2002 SPIE Medical Imaging Meeting: Ultrasonic Imaging and Signal Processing, 2002, pp. 25-36.

Haider, B., "Synthetic Transmit Focusing for Ultrasound Imaging", 2000 IEEE Ultrasonics Symposium, 2000, pp. 1215-1218.

Hergum, T., et al., "Parallel Beamforming using Synthetic Transmit Beams", 2004 IEEE International Ultrasonics, Ferroelectrics, and Frequency Control Joint 50th Anniversary Conference, 2004, pp. 1401-1404.

Nitzpon, P., et al., "New Pulsed Wave Doppler Ultrasound System to Measure Blood Velocities Beyond the Nyquist Limit," 1995, IEEE Transactions Ultrasonics and Ferroelectrics, and Frequency Control, vol. 42, No. 2, pp. 265-279.

Robinson, B., et al., "Synthetic Dynamic Transmit Focus", 2000 IEEE Ultrasonics Symposium, pp. 1209-1214.

Tortoli, P., et al., "Velocity Profile Reconstruction Using Ultrafast Spectral Analysis of Doppler Ultrasound," IEEE Transactions Sonics and Ultrasonics, Jul. 1985, vol. SU-32, No. 4, pp. 555-561.

International Search Report and Written Opinion of Apr. 3, 2008 for PCT Application No. PCT/US07/81253, 9 pages.

Office Action of Nov. 5, 2010 for U.S. Appl. No. 12/628,169, 8 pages.

Office Action of Aug. 3, 2010 for U.S. Appl. No. 11/586,212, 8 pages.

Office Action of Jun. 24, 2010 for U.S. Appl. No. 11/492,471, 11 pages.

Office Action of Dec. 2, 2008 for U.S. Appl. No. 10/961,709, 4 pages.

Office Action of Sep. 14, 2007 for U.S. Appl. No. 10/961,709, 6 pages.

Notice of Allowance of May 15, 2009 for U.S. Appl. No. 10/961,709, 8 pages.

* cited by examiner

ABERRATION CORRECTION USING CHANNEL DATA IN ULTRASOUND IMAGING SYSTEM

CROSS-REFERENCES TO RELATED APPLICATIONS

This application claims the benefit of U.S. Provisional Patent Application No. 60/701,635, filed Jul. 22, 2005, the entire disclosure of which is incorporated herein by reference.

BACKGROUND OF THE INVENTION

This invention relates generally to ultrasound imaging systems and, more particularly, to adaptive optimization of ultrasound imaging system parameters by making use of stored channel data.

Medical ultrasound imaging systems need to support a set of imaging modes for clinical diagnosis. The basic imaging modes are timeline Doppler, color flow velocity and power mode, B-mode, and M-mode. In B-mode, the ultrasound imaging system creates two-dimensional images of tissue in which the brightness of a pixel is based on the intensity of the return echo. In color flow imaging mode, the movement of fluid (e.g., blood) or tissue can be imaged. Measurement of blood flow in the heart and vessels using the Doppler effect is well known. The phase shift of backscattered ultrasound waves can be used to measure the velocity of the moving tissue or blood. The Doppler shift may be displayed using different colors to represent speed and direction of flow. In the spectral Doppler imaging mode, the power spectrum of these Doppler frequency shifts is computed for visual display as velocity-time waveforms.

State-of-the-art ultrasound scanners may also support advanced or emerging imaging modes including contrast agent imaging, 3D imaging, spatial compounding, and extended field of view. Some of these advanced imaging modes involve additional processing of images acquired in one or more basic imaging modes, and attempt to provide enhanced visualization of the anatomy of interest.

A new trend in ultrasound technology development is the emergence of compact or portable ultrasound scanners that leverage the unceasing advances in system-on-a-chip technologies. It is anticipated that these compact scanners, though battery-operated, will support more and more of the imaging modes and functions of conventional cart-based scanners.

Regardless of physical size, ultrasound imaging systems are comprised of many subsystems. In a typical ultrasound imaging system, the main signal path includes the transducer, transmitter, receiver, image data processor(s), display system, master controller, and user-input system. The transducer, transmitter, and receiver subsystems are responsible primarily for the acquisition, digitization, focusing and filtering of echo data. The image data processor performs detection (e.g., echo amplitude for B-mode, mean velocity for color flow mode), and all subsequent pixel data manipulation (filtering, data compression, scan conversion and image enhancements) required for display. As used herein, the term pixel (derived from "picture element") image data simply refers to detected image data, regardless of whether it has been scan converted into an x-y raster display format.

Conventional ultrasound systems generally require optimal adjustments of numerous system parameters involved in a wide range of system operations from data acquisition, image processing, and audio/video display. These system parameters can be divided into two broad categories: 1) user-selectable or adjustable; and 2) engineering presets. The former refers to all system parameters that the user can adjust via the user control subsystem. This includes imaging default parameters (e.g., gray map selection) that the user can program via the user control subsystem and store in system memory. In contrast, "engineering presets" refer to a wide range of system processing and control parameters that may be used in any or all of the major subsystems for various system operations, and are generally pre-determined and stored in system memory by the manufacturer. These may include control or threshold parameters for specific system control mechanisms and/or data processing algorithms within various subsystems.

The need to optimize both kinds of system parameters is a long-standing challenge in diagnostic ultrasound imaging, mainly because (1) the majority of sonographers or users often lack the time and/or training to properly operate a very broad range of user-controls for optimal system performance; and (2) engineering presets are usually pre-determined by the manufacturer based on "typical" or "average" system operating conditions including patient type (body size and fat/muscle composition), normal and abnormal tissue characteristics for various application types, and environmental factors (e.g., ambient light condition).

For a compact scanner, user-control design is particularly challenging because the space available on the console for imaging control keys can be very limited. This means that the overall user-control subsystem will be restricted and/or more difficult to use (e.g., accessing multiple layers of soft-key menus) compared to conventional cart-based scanners.

Another related challenge for all ultrasound scanners is ergonomics. Even for an expert sonographer who is proficient at using all of the available system controls, the repetitive hand motions required to scan with an ultrasound probe, and to adjust many control keys for each ultrasound examination protocol, are widely recognized as a source of repetitive stress injuries for sonographers.

Therefore, there is a need for more automated control of imaging parameters in ultrasound systems.

BRIEF SUMMARY OF THE INVENTION

Embodiments of the present invention provide an ultrasound scanner equipped with an image data processing unit that can perform adaptive parameter optimization during image formation and processing. An exemplary embodiment employs a figure of merit scheme for optimizing one or more imaging parameters. The imaging parameters that may be optimized include system timing and control parameters as well as user-specified processing parameters. One of the key parameters is the speed of sound assumed by the imaging system for transmit and receive focusing. Other parameters include, for example, receive aperture, coherence factor, and the like.

In accordance with an aspect of the present invention, a method of processing data for generating an ultrasound image comprises obtaining channel data by digitizing ultrasound echo data produced by individual transducer elements on an ultrasound scanner in performing an image scan; storing the channel data in a memory; reconstructing an ultrasound image for each of a plurality of trial values of at least one parameter to be optimized using the stored channel data in the memory; evaluating the image quality of the reconstructed ultrasound image for each trial value of the at least one parameter; and determining the optimized value of the at least one parameter based on the evaluated image quality. The channel data may be digitized RF echo data, digitized baseband echo data, or in some other suitable form.

In some embodiments, evaluating the image quality comprises computing a figure of merit for the reconstructed ultrasound image for each trial value of the at least one parameter. The method may further comprise performing actual imaging using the optimized value of the at least one parameter to produce an image frame. The obtaining, storing, reconstructing, evaluating, and determining may be performed in real time. The at least one parameter includes one or more of: the sound speed being used to process the channel data to produce an image frame from the image scan; transmit control parameters for a transmitter of the ultrasound scanner to specify at least one of transmit waveform, aperture function, delay profile, and pulsed repetition frequency for one or more imaging modes; electronic array focusing parameters for a receiver of the ultrasound scanner to specify at least one of front end filter, front end gain, and receive aperture function as a function of time/depth and the time delay profiles for image reconstruction; or image processing parameters for an image data processor of the ultrasound scanner to specify at least one of display dynamic range, gray or color maps, and spatial/temporal filtering.

In specific embodiments, evaluating the image quality comprises selecting an image region for evaluation. Evaluating the image quality comprises computing one or more image focus quality parameters; and determining the optimized value comprises determining the optimal value of the at least one parameter to be optimized by comparing the one or more image focus quality parameters. The one or more image focus quality parameters are used to maximize an overall lateral spatial resolution of the selected image region due to improved focusing. Computing one or more image focus quality parameters comprises providing a focus quality spectrum.

In some embodiments, multiple sets of channel data are obtained, stored, and processed by the reconstructing, evaluating, and determining. The method further comprises computing a figure of merit for the reconstructed ultrasound image for each trial value of the at least one parameters, for each set of channel data; and combining the figure of merits for the multiple sets of channel data to provide a combined figure of merit.

In accordance with another aspect of the invention, an ultrasound system comprises a channel data memory to store channel data obtained by digitizing ultrasound echo data produced by an image scan; an image data processor configured to process the stored channel data in the memory to reconstruct an ultrasound image for each of a plurality of trial values of at least one parameter to be optimized; and a parameter optimization unit configured to evaluate an image quality of the reconstructed ultrasound image for each trial value of the at least one parameter, and to determine the optimized value of the at least one parameter based on the evaluated image quality.

In accordance with another aspect of the present invention, an ultrasound system comprises a channel data memory to store channel data obtained by digitizing ultrasound echo data produced by an image scan; an image data processor configured to process the stored channel data in the memory to reconstruct an ultrasound image for each of a plurality of trial values of at least one parameter to be optimized; and a parameter optimization unit including a parameter optimization program stored in a computer readable storage medium. The parameter optimization program includes code for evaluating an image quality of the reconstructed ultrasound image for each trial value of the at least one parameter, and code for determining the optimized value of the at least one parameter based on the evaluated image quality.

DETAILED DESCRIPTION OF THE INVENTION

Figure 1:
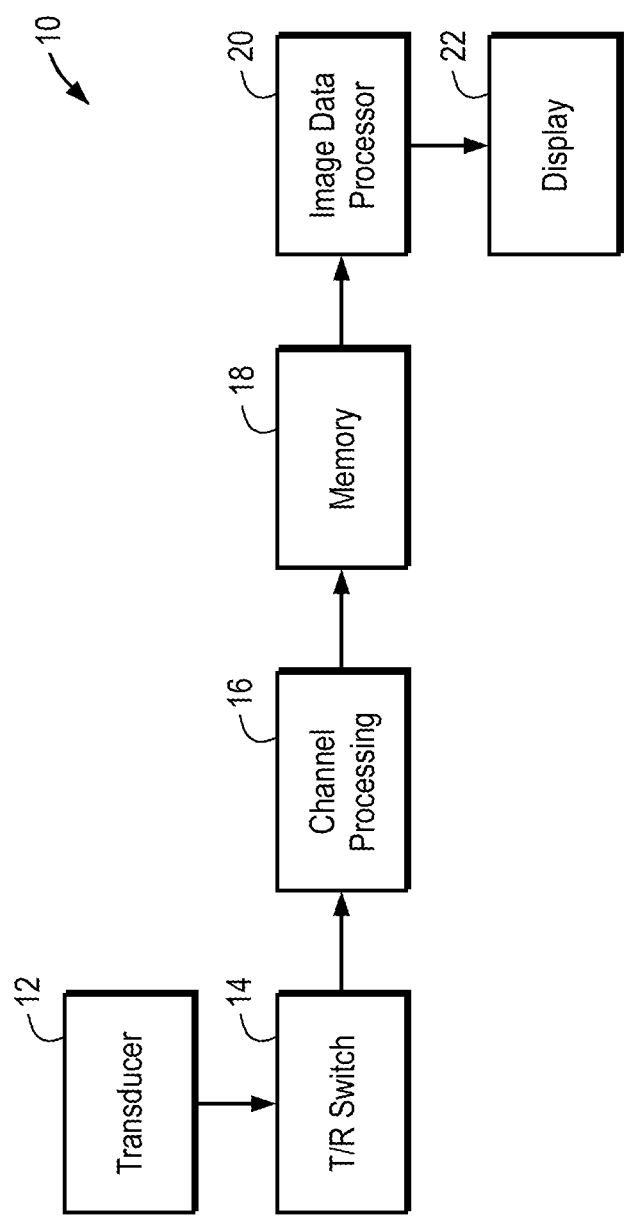
FIG. 1 is a block diagram of the system architecture of an ultrasound scanner according to an embodiment of the present invention.

FIG. 1 is a block diagram of the system architecture of an ultrasound scanner 10. In a specific embodiment, the scanner 10 employs a zone-based technique for real-time B-mode imaging, and utilizes a transmit beam from which many receive beams are formed, such that a full field of view image can be formed using much fewer firings than a conventional system, i.e., 30-50 firings. The main signal path begins with a transducer 12 with switch 14. The transducer 12 includes an array of transducer elements. For each transmit beam firing, the receive RF echo data is digitized and preprocessed within the channel processing block 16 where demodulation, averaging, and filtering occurs. Next, the baseband channel in-phase/quadrature (I/Q) data is stored in a large memory 18. An image data processor 20 (e.g., one or more DSPs or Digital Signal Processors) pulls the channel I/Q data from the memory 18, and performs dynamic receive beam formation, detection, log compression, filtering, and scan conversion. Beam formation is the process by which the signals on individual channels, each received from a different transducer element, are combined to form a single signal representative of the echoes received from the body by the defined transducer aperture. In CD/PW modes, Doppler processing is performed as well. According to this system architecture, channel I/Q data storage in the memory 18 allows acquired data to be reprocessed by the DSP or processor 20 multiple times to extract additional information (i.e., compounding).

In subsequent SW beam formation and image processing, the raw channel data is reused which provides a good match to current DSP memory and caching architectures, while the FPGA front-end and DSP implementation provide increased development flexibility. Furthermore, channel data storage provides offline Matlab processing of multiple frames of acquired I/Q channel data, which can be used in verifying the SW system processing chain, algorithm development with real static and dynamic data, and as a research tool. The result of the processing is sent to a display unit 22 such as an LCD or CRT monitor.

Signal processing in the ultrasound scanner begins with waveform shaping and delay of the excitation pulses applied to each element of a transducer array to generate a focused, steered, and apodized pulsed wave that propagates into the body. Many characteristics of the transmitted acoustic pulse are adjusted in such a manner to be closely linked with some adjustment in the receive signal processing, the simplest link being the setting of a particular imaging mode. For example, standard pulse shaping adjusts the pulse length for a given transmit firing depending upon whether the returned echoes are ultimately to be used for B-mode, pulsed Doppler, or color Doppler imaging. Equally critical is the center frequency of the pulse which, for modern broadband transducers, can be set over a wide range, applicable to the part of the body being scanned. Some scanners also routinely shape the envelope of the pulse to improve the propagation characteristics of the resulting sound wave.

One of the adjustable parameters that affect image formation is the system assumed sound speed. Echoes resulting from scattering of the sound by tissue structures are received by all elements within the transducer array. Processing of these echo signals routinely begins at the individual channel (element) level with the application of apodization functions, dynamic focusing and steering delays, and frequency demodulation to reduce the cost of the former. Knowledge of the speed of sound is important. Typically, a nominal sound speed is used, e.g., 1.54 mm/µs, which is the value assumed by most systems. The error between the actual and assumed sound speed is one source of aberration in the detected image and leads to defocusing and increased acoustic clutter noise. The present invention provides a technique of correcting aberration caused by sound speed errors by optimizing the system assumed sound speed estimation using the channel data. In addition, the optimized system assumed sound speed for the focusing and steering delays can be separate from the sound speed used for image display, so as to maintain image registration if desired, thus avoiding image contraction or expansion due to different system assumed sound speeds. As a result, the transmit/receive focusing is altered based on the determined optimal sound speed, while maintaining the image scaling in spite of the sound speed change. The technique can be used for parameter optimization of other imaging parameters in the scanner system including, for example, receive delay profile, receive aperture, coherence factor, and the like.

Figure 2:
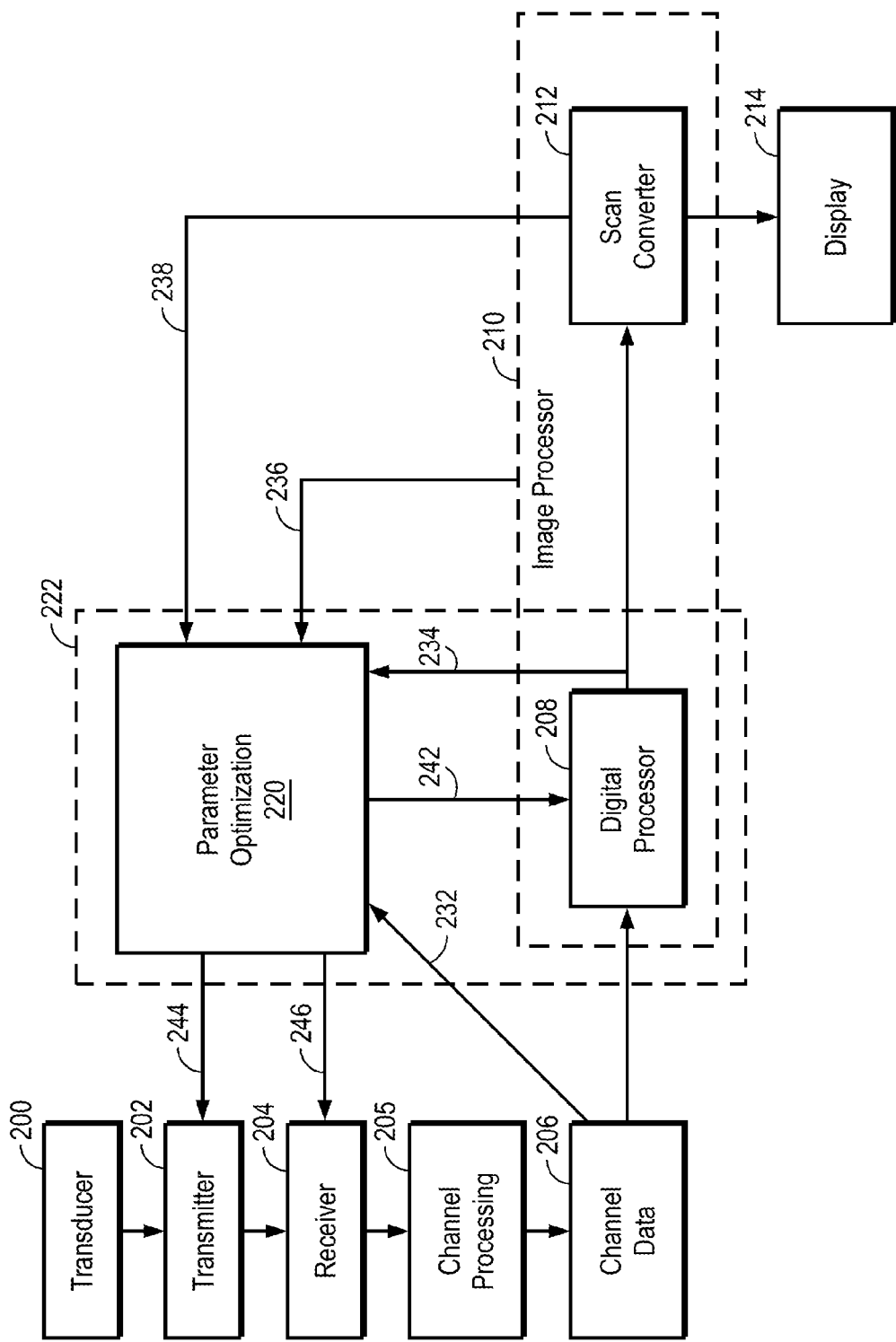
FIG. 2 is a diagram of the main image data processing blocks of the ultrasound scanner according to an embodiment of the present invention.

FIG. 2 shows a diagram of the main image data processing blocks of the ultrasound scanner. A transmitter 202 causes the transducer 200 to be energized and produce signals that are received by a receiver 204. Channel data is processed in the channel processing block 205 and saved in the channel data memory 206. The channel data can be processed, repeatedly if desired, by the digital processor 208, which performs dynamic receive beam formation, detection, log compression, filtering, and the like. Image processing is performed in the image processing block 210, which includes digital processing in the digital processor 208 and scan conversion in the scan conversion block 212. The image is displayed on the display 214. A parameter optimization block 220 is provided for imaging parameter optimization. The parameter optimization block 220 and the digital processor 208 may typically be configured as a digital processing block 222 that digitally processes the channel data and produces imaging data to be used to form the image for display.

The parameter optimization block 220 performs parameter optimization using any desired approach. In an exemplary embodiment, a figure of merit scheme is employed. The scheme takes one or more inputs and calculates a figure of merit based upon estimated values of one or more parameters. The goal is to optimize the focus quality of the image by iteratively varying one or more imaging parameters according to the figure of merit scheme. Advantageously, the channel data is stored in the memory 206 and can be used repeatedly to calculate the figure of merit in the parameter optimization block 220 (see arrow 232). Other inputs may include, for example, beam formation data after beam forming in the digital processor 208 (arrow 234), acoustic data after image processing 210 (arrow 236), and scan converted data after scan conversion 212 (arrow 238). Based on the figure of merit calculation performed by the parameter optimization block 220, one or more parameters may be adjusted, including the speed of sound used in the digital processor 208 to process the data (arrow 242). Examples of other parameters that may be adjusted include image processing parameters for the digital processor 208 to specify at least one of display dynamic range, gray or color maps, and spatial/temporal filtering (arrow 242); transmit control parameters for the transmitter 202 to specify at least one of transmit waveform, aperture function, delay profile, pulsed repetition frequency for one or more imaging modes, and transmit waveform characteristics (arrow 244); electronic array focusing parameters for the receiver 204 to specify at least one of front end filter, front end gain, and receive aperture function as a function of time/depth and the time delay profiles for image reconstruction (arrow 246); and a control logic module in the parameter optimization block 220 can be used to make these adjustments.

Figure 3:
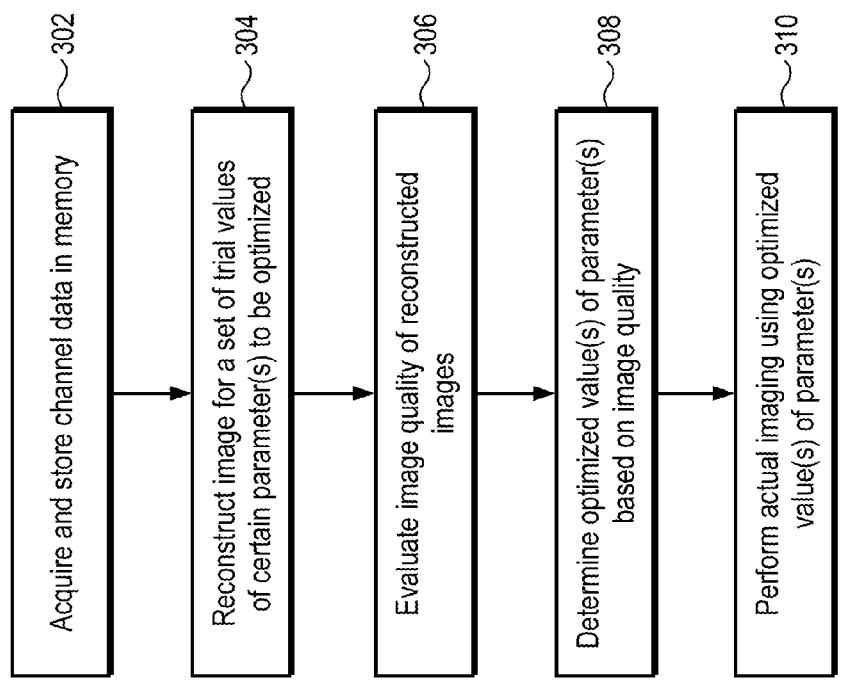
FIG. 3 is a flow diagram of the parameter optimization procedure according to an embodiment of the present invention.

The parameter optimization procedure is summarized in the flow diagram of FIG. 3. The channel data is acquired and stored in the memory 206 (step 302). Iterative or trial values of certain parameter(s) are used to reconstruct the image of interest by the digital processor 208 and scan converter 212 which comprise the image data processor (step 304). One parameter may be the speed of sound. The image quality such as focus quality of the image generated is evaluated in step 306. For instance, this may involve the calculation of a figure of merit. Based on the evaluation, an optimized value for each parameter of interest is obtained in step 308. In step 310, actual imaging is performed using the optimized value(s) to produce the image of interest. In addition, the optimized value(s) determined using one or more system modes, can be used in other system modes. For example, optimal parameter(s) determination using B-mode channel data may then be used to improve color doppler imaging (velocity, power), spectral doppler (PW), etc., in addition to the B-mode image. The procedure can then be repeated for the next image frame. If the image data acquisition and processing time combined with the parameter optimization time is within the frame time for the image frame, then parameter optimization can be performed in real time. Otherwise, there will be a delay in the image reconstruction for the image frame.

The parameter optimization procedure is preferably automated and programmed into the hardware and/or software of the ultrasound scanner. The computer program is stored in a computer-readable storage medium and executed by a computer processor. The user can optimize the image by pressing an auto-optimization button of the ultrasound scanner. Real time processing is desirable but not required.

In the ultrasound scanner of FIG. 2, a complete scan is performed by acquiring a series of echoes in which switches are set to their transmit position, the transmitter 202 is gated ON momentarily to energize each transducer element of the transducer 200, the switches are then set to their receive position, and the subsequent echo signals detected by each transducer element are applied to receiver 204, which amplifies, filters, digitizes and combines the separate echo signals from each transducer element to produce a set of echo-location image data. Within the receiver 204, the echo-location image data may be down-shifted in frequency to produce their in-phase/quadrature (I/Q) components. Depending on the scan mode, the I/Q data is converted into respective B, color flow, B flow or spectral Doppler images in the scan converter 212, which outputs raster-scan images to the display unit 214.

The parameter optimization block 220 is configured to perform image optimization functions. Specifically, based on pixel image data from the image data processor (digital processor 208 and scan converter 212), the parameter optimization block 220 can automatically adjust parameters in the transmitter 408, receiver 404, and/or image data processor directly through signal/data paths. By automating the user-controls based on actual image data, the efficiency, reproducibility, and ease of use of ultrasound scanner can be significantly enhanced.

An example of an automatic sound speed correction algorithm is used to illustrate the parameter optimization methodology. It is meant to be representative, but not exhaustive, of the capabilities of adaptive parameter optimization method of the present invention.

Figure 4:
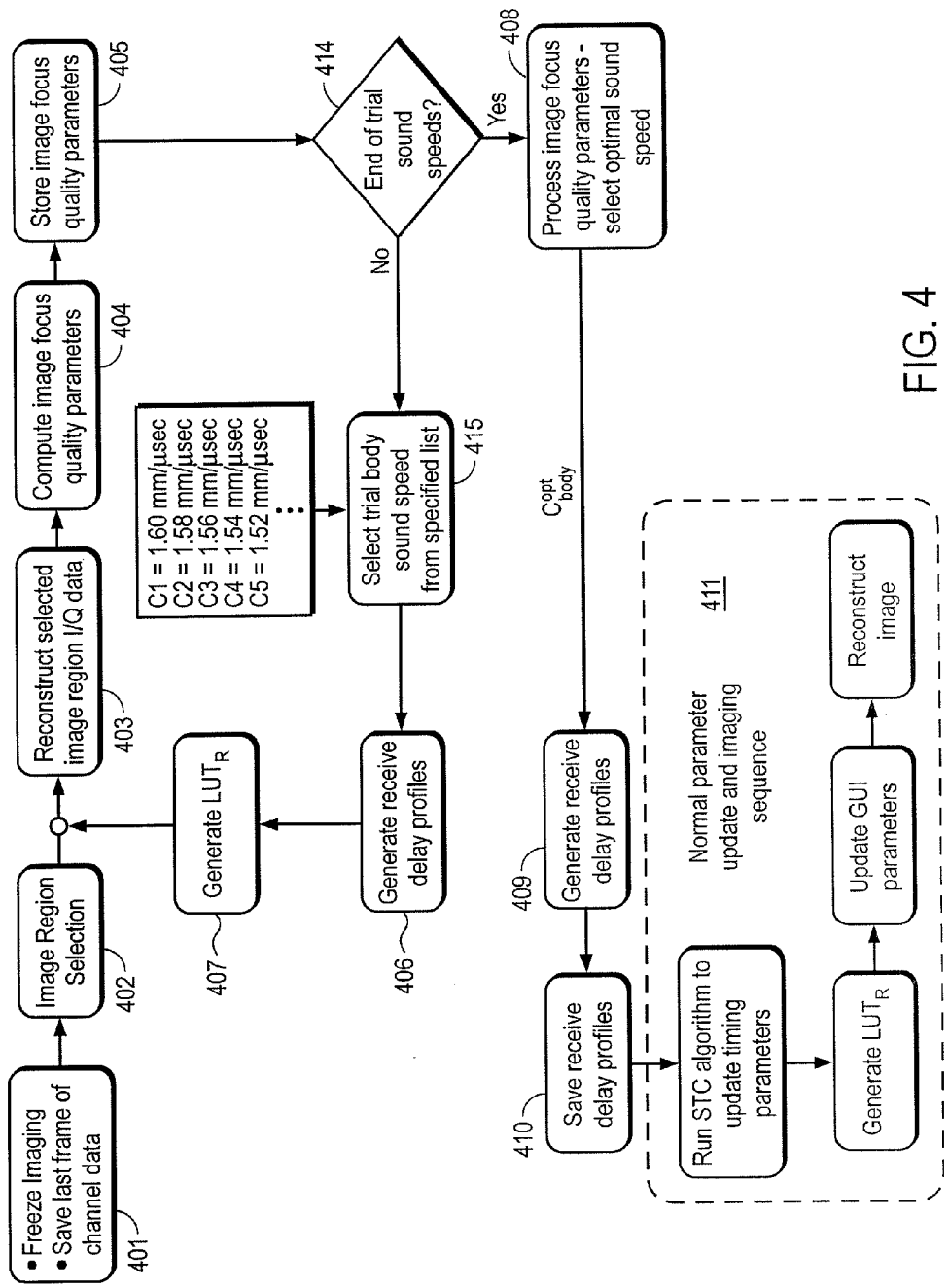
FIG. 4 is a block diagram of the automatic sound speed correction (SSC) algorithm according to a specific embodiment of the present invention.

FIG. 4 shows a block diagram of the automatic sound speed correction (SSC) algorithm according to a specific embodiment of the present invention. The basic idea is that the user, upon wanting to optimize the image for the body sound speed for a given region of anatomy, presses a user interface (UI) "auto optimize" button. The system freezes live imaging, runs the auto SSC algorithm to estimate the overall body sound speed which produces the optimum image quality from the user selected imaging region, re-computes the receive (and potentially transmit) delay profiles, and returns the user to live imaging within a short amount of time. By determining and correcting for the overall body sound speed, a 1st order aberration correction is achieved—in particular, bulk sound speed errors are minimized or eliminated. Note that since the random delay variations introduced across the array by the particular body anatomy/probe geometry frame-to-frame varying relationship are not addressed, the SSC algorithm does not have to run at real-time frame rates. It only needs to run within a tolerable user response time, on the order with other UI response times such as depth change, etc. Once optimized, the estimated sound speed should be optimal for the anatomy being imaged, even for different views, as indicated from recent experiments. Note that while the SSC algorithm executes, the user does not need to hold the probe still since the ultrasound imaging system captures and stores channel data and can be reprocessed as much as desired, in contrast with conventional systems which would have to continue to capture beamformed data for each reprocessing step, thus simplifying the procedure for the user. If the user had kept the ultrasound probe in approximately the same location, the change in the image for a particular region can be visualized.

The process of freezing live imaging and storing a frame of channel data is performed in block 401. In the image region selection block 402, the region for estimating the body sound speed is selected. Block 403 reconstructs the selected image region. Block 404 computes the focus quality parameters which allow the SSC algorithm to estimate the body sound speed in a subsequent step. Block 405 involves storing the focus quality parameters. Block 406 generates the receive reference delay profiles from a sound speed specified in a search list and used in constructing the reconstruction look-up table $LUT_R$. The reconstruction look-up table $LUT_R$ contains receive beamformation parameters such as channel, range, and line dependent delay, phase, apodization profiles, gains, etc. Block 407 generates the reconstruction look-up table $LUT_R$. Block 408 processes the focus quality parameters to determine the best estimate of the body sound speed for the region of the body selected. Blocks 409, 410, and 411 involve generating and saving the receive reference delay profiles using the estimated body sound speed, re-running the SSC algorithm to produce new timing parameters, generating the reconstruction look-up table $LUT_R$, updating any GUI parameters needed, and finally, returning the user to live imaging. These blocks are discussed in greater detail below.

In block 401, upon activation of the "optimize" button, or suitable user control, the system will freeze imaging, leaving the last multi-mode frame processed, i.e., B/CD-mode, etc., frozen on the display. In one implementation, digital signal processors will store/retain the last frame's B-mode channel data only into an external memory unit for sound speed reprocessing.

In block 402, the region of the image to be used by SSC algorithm is controlled by parameters specified in the database. While the entire current image region can be used by the SSC algorithm to determine the optimal sound speed, pre-specified parameters place constraints on the region of the image utilized in order to aide the SSC algorithm and make it more robust, as well as minimize computation time. The parameters could include, for example, minimum start depth, image width fraction, image range fraction, minimum number of lines, minimum number of range samples, etc.

For the minimum start depth, it has been found through experimentation on channel datasets obtained from phantoms as well as from the body, that the region of the image less than about 5 mm does not demonstrate good sound speed specificity across a wide range of sound speeds. This is most likely due to the fact that there are not many receive channels on for the transducers used, and due to the timing error being cumulative, proportional to the round-trip time, i.e., $$t_{error} = t\left(1 - \frac{c_{acutal}}{c}\right),$$

however this can vary based upon the transducer's actual geometry.

The image width fraction is used to exclude the edges of the image which may be generated from portions of the transducer which may not have good contact (note that this may be more useful for curved arrays). This can also be used to reduce the computation time for the $LUT_R$, however, at the expense of possibly excluding potential target areas necessary for a good estimate of the sound speed by the SSC algorithm. The image range fraction is used to exclude the beginning and ending regions of the image, mainly to reduce computation time for the $LUT_R$, however, at the expense of possibly excluding potential target areas necessary for a good estimate of the sound speed by the SSC algorithm. This is applied on the region prior to the application of the minimum start depth. The minimum number of lines is used, in conjunction with the other constraints, to limit how small the SSC region in the lateral direction can be and still produce accurate sound speed estimates. The minimum number of range samples is used, in conjunction with the other constraints, to limit how small the SSC region in the range direction can be and still produce accurate sound speed estimates.

In block 403, using the generated reconstruction $LUT_R$, the selected SSC image region is reconstructed and I/Q data is produced. Note that the reconstructed range limits are determined by the current displayed range limits and the trial sound speed being used to evaluate the focus quality parameters. The line limits are determined by pre-specified constraints.

In block 404 involving the computation of image focus quality parameters, the SSC algorithm seeks to determine the optimal system sound speed which maximizes the overall lateral spatial resolution of the selected image region due to improved focusing, under the assumption that this system sound speed represents the best estimate for the overall body sound speed. There are many ways in which to determine the lateral spatial resolution, for example, imaging point and/or wire targets contained in a phantom. Quantifying the spatial resolution can be performed in either the lateral spatial domain directly, or in the spatial spectral domain. Because the body does not contain point targets in general, one must be content with determining and quantifying the lateral spatial resolution from point-like structures, speckle, contrast lesions, etc. Therefore the question becomes whether a technique can be found to extract the improvement in image quality and hence, lateral spatial resolution, from both phantoms and real-world body images, as the system sound speed is varied. Through experimentation on both phantom images as well as body images across several imaging applications, it has been found that a reasonable measure of image quality improvement or degradation as the system sound speed is varied through modification of the receive delays, consists of a) averaging lateral spatial spectra across range for each trial sound speed to produce a representative spatial spectrum (computed on a suitably detected I/Q image), and b) integrating each spectrum across a specified set of spatial frequencies producing the total energy—a single number indicating the focus quality of the image for each trial sound speed, defined as $Q_f(c)$. The idea is that any overall increase in the spectral density (and subsequently energy) as the sound speed used for receive focusing is varied—broadening the average lateral spatial spectrum, the better the focusing and spatial resolution. This approach is useful only to the extent that an increase in the focus quality $Q_f(c)$ is well correlated with observed improvements in lateral spatial resolution and contrast.

Several different focus quality spectrum $Q_f(s,c)$ definitions were examined and compared to each other using both phantom images and body images. They were:

$$\text{Square of Sums} - Q_f(s, c) = \left[ \frac{1}{N_r} \sum_{r=r_1(c)}^{r=r_2(c)} |FFT\{|z_{IQ}(r, usl, c)|^2\}| \right]^2 \quad \text{(a)}$$

$$\text{Sum of Squares} - Q_f(s, c) = \frac{1}{N_r} \sum_{r=r_1(c)}^{r=r_2(c)} |FFT\{|z_{IQ}(r, usl, c)|^2\}|^2 \quad \text{(b)}$$

$$Q_f(s, c) = \frac{1}{N_r} \sum_{r=r_1(c)}^{r=r_2(c)} |FFT\{z_{IQ}(r, usl, c)\}|^2 \text{ or} \quad \text{(c)}$$

$$\frac{1}{N_r} \left[ \sum_{r=r_1(c)}^{r=r_2(c)} |FFT\{z_{IQ}(r, usl, c)\}| \right]^2$$

where $z_{IQ}$ is the reconstructed I/Q image region, $N_r$ is the number of range samples averaged from starting range $r_1(c)$ to ending range $r_2(c)$—both a function of the trial sound speed in order to ensure that the same collection of scatterers, i.e., image features, are analyzed (since the image will be contracted or expanded due to the mapping of time t into range r through sound speed c, i.e., r=ct/2), and where FFT{•} indicates a lateral spatial transform across usl (ultrasound line) with an appropriate amount of zero padding to a power of 2 number of lines, i.e., 256, 512, etc., and s is the normalized spatial frequency. This produces a spatial spectrum as a function of trial sound speed c as shown in FIG. 5 for detection technique (a), i.e., Square of Sums, for a wire target phantom and an OB case.

Prior to plotting each spectrum in dB, each has been normalized by its maximum value and in addition, the normalized spectrum computed for sound speed 1.54 mm/μsec was subtracted (in dB) in order to see improvements or degradations from a 1.54 mm/μsec sound speed image (since this is usually the standard sound speed used on most systems). Thus, the plots of FIG. 5 depict the differential spectra $$10\log_{10}\left[\frac{Q_f(s, c)}{\max_s\{Q_f(s, c)\}}\right] - 10\log_{10}\left[\frac{Q_f(s, 1.54)}{\max_s\{Q_f(s, 1.54)\}}\right].$$

Figure 5:
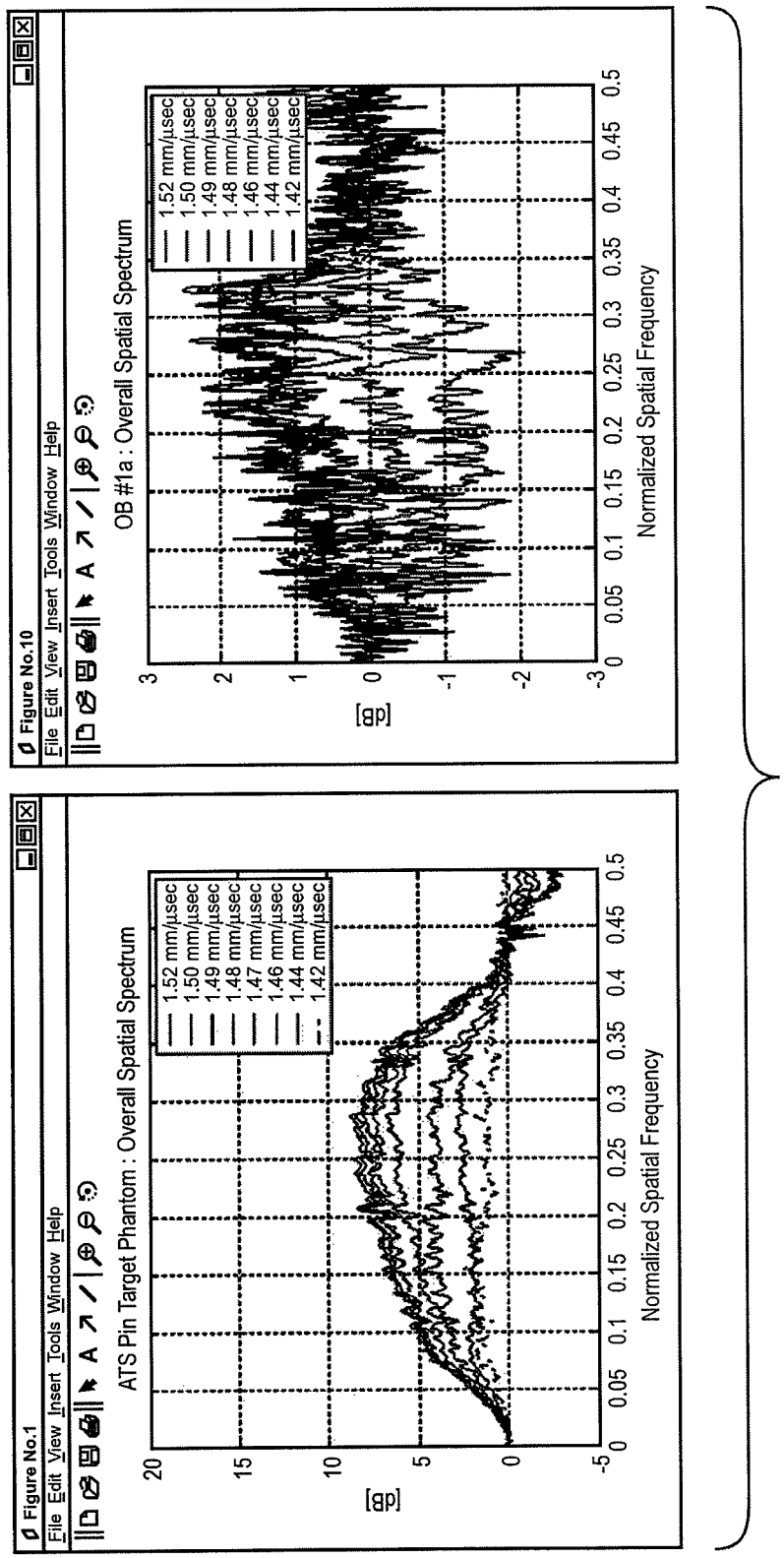
FIG. 5 shows a spatial spectrum as a function of trial sound speed for a square of sums definition for the focus quality spectrum.

Looking at the differential spectra shown in FIG. 5 for the phantom, it can be seen that the differential spectrum with the highest energy, indicating the broadest spectrum, is for trial sound speed of 1.48 mm/μsec. For the OB spectra, the differential spectrum with the highest energy is for trial sound speeds 1.48 mm/μsec-1.49 mm/μsec. In both of these examples, images reconstructed for these trial sound speeds were judged to have the best overall image quality.

Figure 6A:
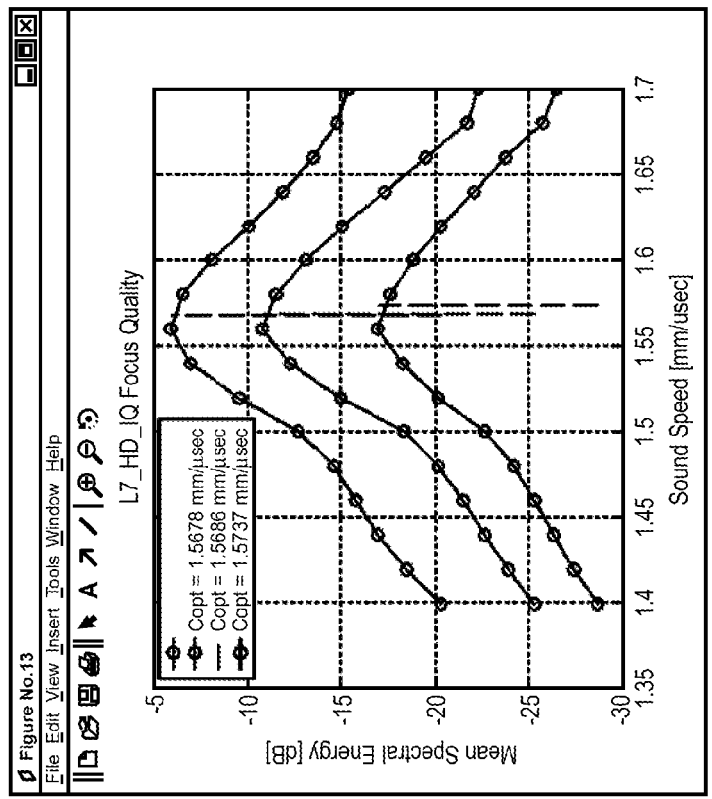
FIGS. 6A-6C show focus quality plots using different focus quality spectrum definitions, including "square of sums," "sum of squares," and one based upon the transform of the image I/Q data directly.
Figure 6B:
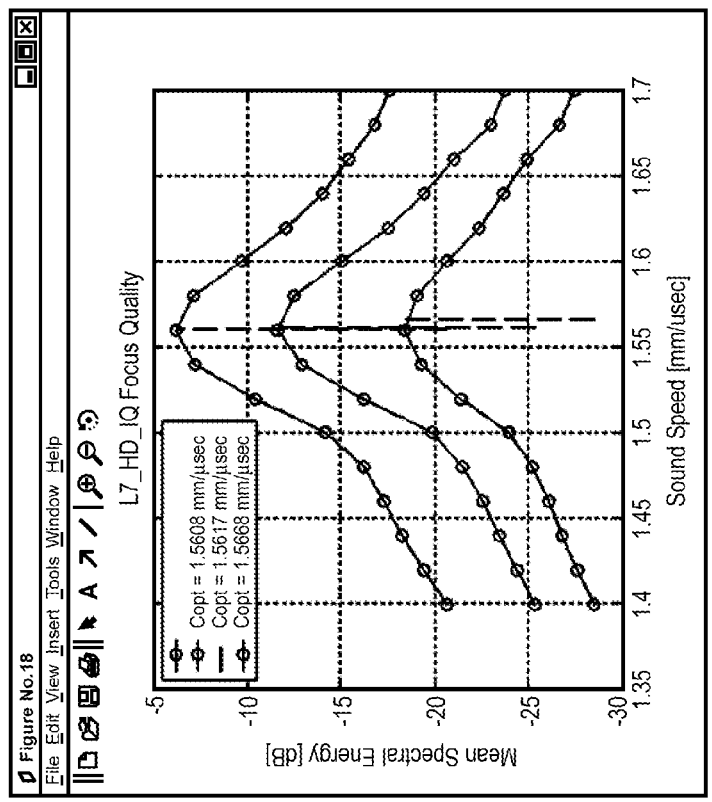
Figure 6C:
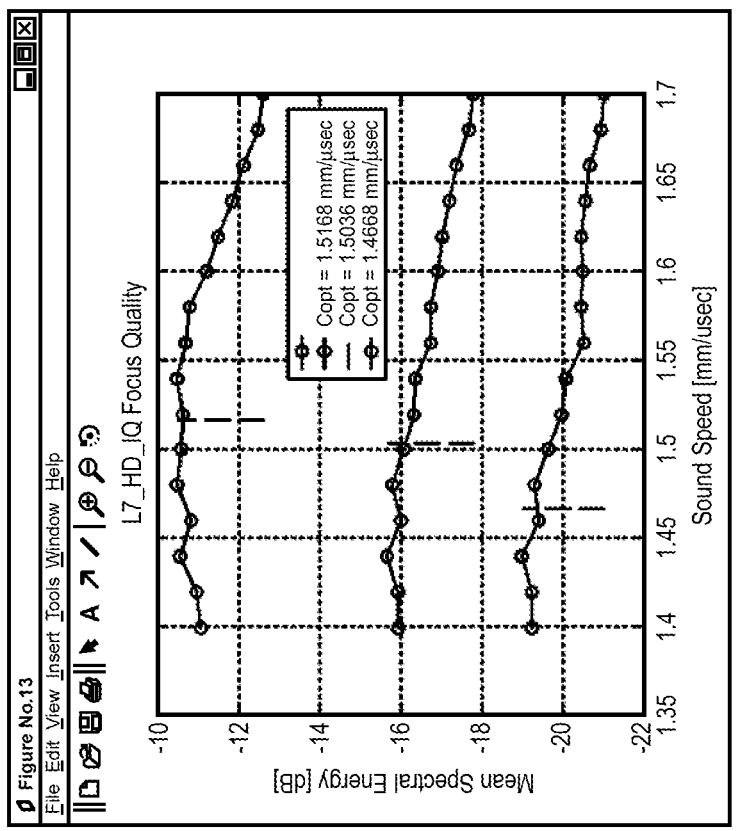

For each of these focus quality spectra $Q_f(s,c)$ definitions, the focus quality $Q_f(c)$ was computed by averaging $Q_f(s,c)$ in the log domain, i.e., averaging $Q_{f\_dB}(s,c)$, over the set of spatial frequencies s=0 to s=$s_{max}$, where $s_{max}$ is a predefined value. The choice of performing the integration in the log domain, i.e., in dB, was based upon the empirical observation of more consistent sound speed results in the same anatomy from different views, in cases where the focus quality contrast, defined as max $\{Q_f(c)\}$-min$\{Q_f(c)\}$, was low. This may be due to the fact that by integrating in the log domain, relative changes are being equally emphasized. The example seen in FIGS. 6A, 6B, and 6C show the focus quality factor $Q_f(c)$ plotted as a function of c for the high dynamic range wire target phantom, where $s_{max}$ assumes the values of {0.2, 0.3, 0.4}. In each case, the optimum overall speed of sound reported was computed by taking points which were above 25% of the focus quality contrast, i.e., max $\{Q_f(c)\}$-min$\{Q_f(c)\}$, over the range of trial sound speeds c used, and taking the centroid (where the centroid was computed in the non-log domain).

It can be seen from FIGS. 6A and 6B, that the 'square of sums' and the 'sum of squares' respectively, are about the same, with the 'square of sums' displaying slightly better sharpness over system sound speed. FIG. 6C, which depicts the focus quality based upon the transform of the image I/Q data directly, shows very poor specificity with system sound speed. This is most likely due to the fact that a 1-way defocused beam's spatial spectrum maintains approximately the same amplitude distribution, while only the phase spectrum is distorted due to diffraction. Thus, there will not be a strong broadening of the spatial spectrum as the correct system sound speed is approached, as in the other two candidate focus quality detectors analyzed. Thus, the focus quality detector chosen is:

Square of Sums:

$$Q_f(s,c) = \left[\frac{1}{N_r}\sum_{r=r_1(c)}^{r=r_2(c)}|FFT\{|z_{IQ}(r, usl, c)|^2\}|\right]^2;$$

and $$Q_{f\_dB}(c) = \frac{1}{N_s}\sum_{s=0}^{s=s_{max}}10\log_{10}[Q_f(s,c)] - Q_{f0\_dB}(c)$$

$$Q_{f0\_dB}(c) = 10\log_{10}\{\max_s[Q_f(s,c)]\}$$

$$Q_f(c) = 10^{\frac{Q_{f\_dB}(c)}{10}}$$

where $N_s$ is the number of samples from s=0 to s=$s_{max}$.

In block 405, after computation of the image focus quality parameters $Q_{f\_dB}(c)$, $Q_{f0\_dB}(c)$, $Q_f(c)$, they are stored for each system trial sound speed for subsequent processing. If the end of the trial sound speeds has not been reached (no in step 414), block 415 selects the next trial body sound speed from a specified list and proceeds to block 406.

Block 406 involves generating a receive delay data set. Given a specified trial sound speed, the system needs to create channel, range, and line dependent receive delay profiles for the generation of the reconstruction $LUT_R$. This can be computed in a variety of ways. For example, the receive delays can be computed by the digital processor based upon the transducer geometry, trial sound speed, and image point location. The receive delays can also be computed by interpolating in range, angle, and sound speed from sparsely computed reference delay data sets.

In block 407, upon completion of generating channel, range, and line dependent receive delay profiles for the specified sound speed, the reconstruction $LUT_R$ needs to be generated for the current iteration. This involves several steps.

Figure 7:
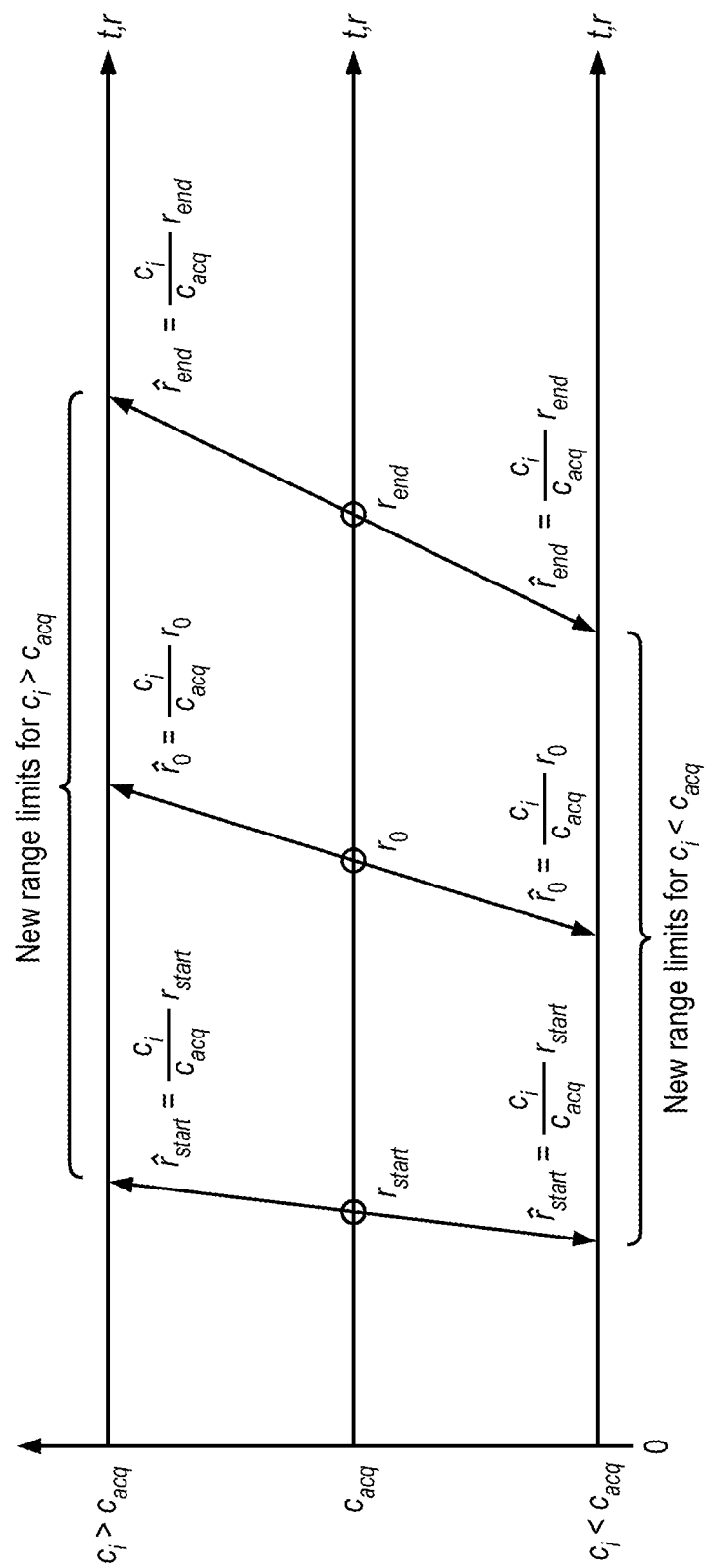
FIG. 7 illustrates the computation of range limits of a sound speed correction image region.
Figure 8:
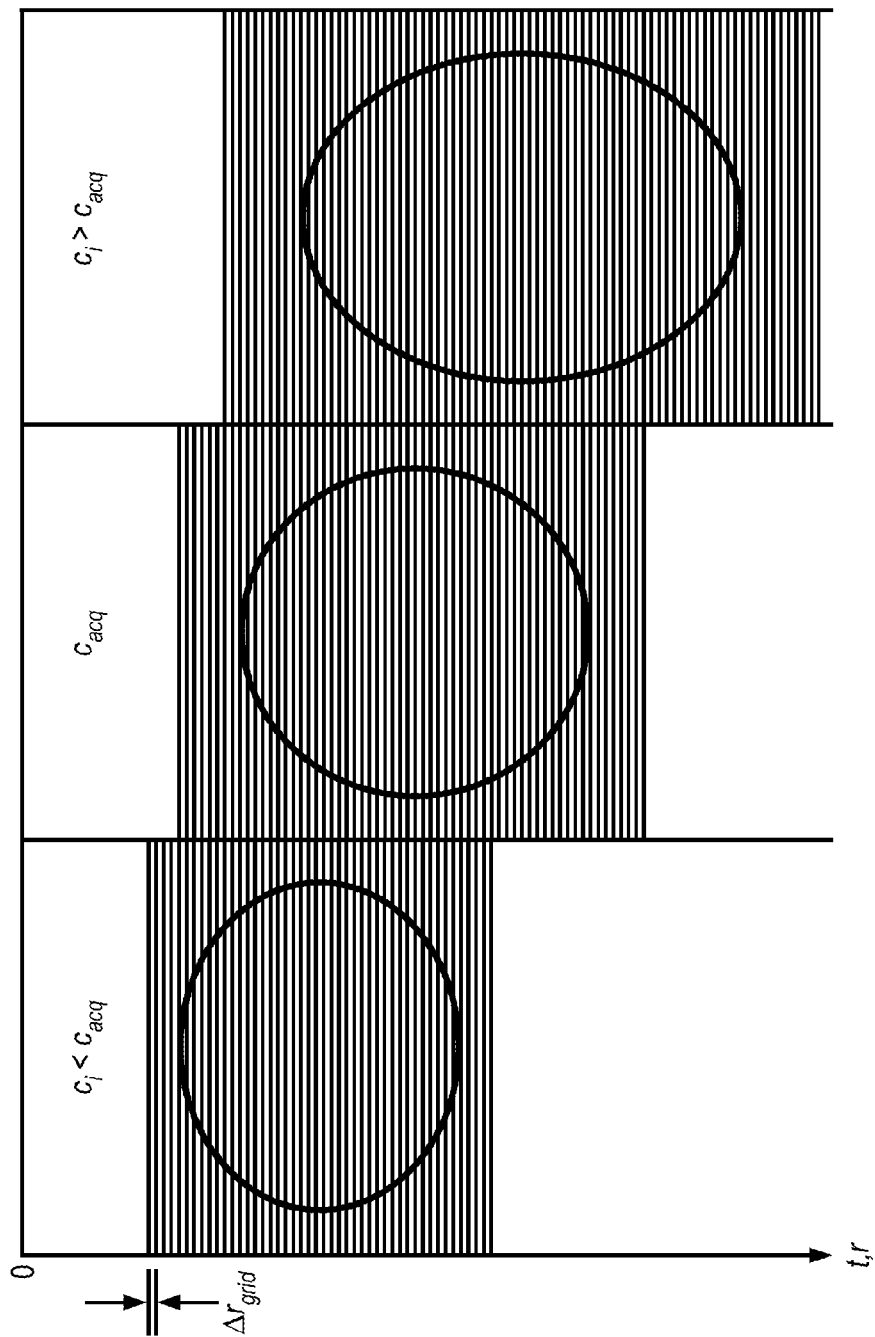
FIG. 8 illustrates the image range contraction/expansion during sound speed correction.

First, the range and line limits of the selected SSC image region need to be computed based upon the current imaging region and pre-specified parameters. The line limits are straightforward, constant throughout SSC iterations, and analogous to how the user zoom box line limits are determined. The range limits are more involved, however. They depend not only upon database specified parameters, but also upon the sound speeds used for data capture and SSC iteration. Thus, the range limits and hence, reconstruction $LUT_R$, will change on each SSC iteration. The range limits for the reconstruction $LUT_R$ are computed in the following manner in order to ensure that the same set of image scatterers are analyzed for each distinct sound speed by the SSC algorithm. This also ensures that the image region ultimately viewed by the user after the SSC algorithm completes the optimization will be the same. Now for a given target return time $t_0$, appearing at range $r_0=c_{acq}t_0/2$, upon using a different sound speed for receive delay computation, the range at which the target will appear is given by $$\hat{r}_0 = \frac{c_i}{c_{acq}}r_0,$$

a simple scaling based upon the ratio of the trial sound speed $c_i$ and the channel data acquisition sound speed $c_{acq}$, as shown in FIG. 7. Thus, for trial sound speeds which are higher than the acquisition sound speed, targets will appear to shift to deeper ranges, the degree of which increases with range. For trial sound speeds which are lower than the acquisition sound speed, targets will appear to shift to shallower ranges, the degree of which increases with range as well. This geometric contraction/expansion is shown in FIG. 8. An image which appears as a circle at the data acquisition sound speed will appear as a flattened ellipse for trial sound speeds less than the data acquisition sound speed, and an elongated ellipse for trial sound speeds greater than the data acquisition sound speed.

The starting and ending ranges, as well as the number of range samples, are given by $$\hat{r}_{start}(c_i, c_{acq}) = \frac{c_i}{c_{acq}}r_{start}(c_{acq}) \quad \hat{r}_{end}(c_i, c_{acq}) = \frac{c_i}{c_{acq}}r_{end}(c_{acq})$$

$$\Delta\hat{r}_{grid}(c_i, c_{acq}) = \frac{c_i}{c_{acq}}\Delta r_{grid}(c_{acq})$$

$$N_r(c_i, c_{acq}) = 1 + \text{round}\left[\frac{\hat{r}_{end}(c_i, c_{acq}) - \hat{r}_{start}(c_i, c_{acq})}{\Delta\hat{r}_{grid}}\right]$$

where $N_r$ is the number of range samples in the reconstruction $LUT_R$ for a given trial sound speed $c_i$, and $\Delta r_{grid}$ is the range grid sample spacing.

The next step is to perform all other reconstruction $LUT_R$ computations as before, which involve computation of the channel, range, and line dependent parameters described previously, computed for the trial sound speed dependent range samples.

In block 408, once all the image focus quality parameters have been computed and stored for all the trial sound speeds specified (yes to step 414), the SSC algorithm will perform the following: 1) determine whether the parameters support a robust sound speed estimate, and 2) if so, compute an optimal sound speed estimate.

In the first step, the focus quality parameters computed, along with any pre-specified parameters, should allow the SSC algorithm to determine whether a robust sound speed estimate is possible. This can be accomplished by comparing de-normalized focus quality maximum $Q_{f\_dB}(c)+Q_{f0\_dB}(c)$ with a pre-specified threshold. If $Q_{f\_dB}(c)+Q_{f0\_dB}(c)$ is below the specified threshold, most likely determined through evaluation and experimentation with noisy images, then the SSC algorithm will conclude that any estimate will not be reliable and therefore, the system should continue to use the data acquisition sound speed and associated receive delay profiles when subsequently returning to live imaging. Other ways in which the SSC algorithm can determine whether a robust sound speed estimate is possible is to consider the focus quality contrast (the difference between the highest and lowest values over the range of trial sound speeds considered during the iteration process), the location of the focus quality $Q_{f\_dB}(c)$ peak (how close it is to the trial sound speed limits), how far above the expected system noise the channel or reconstructed image signals are, etc.

In the second step, when it is determined that the focus quality parameters will produce a reliable optimal sound speed estimate, then the question becomes how to compute an optimal sound speed estimate. While selecting the sound speed location of the total focus quality $Q_{fT\_dB}(c)=Q_{f\_dB}(c)+Q_{f0\_dB}(c)$ peak as the optimal sound speed estimate is appealing at first glance, given that each empirical value of $Q_{fT\_dB}(c)$ has an associated uncertainty contained in it, the location of the peak value may not produce the best estimate. In addition, the total focus quality $Q_{fT\_dB}(c)$ peak may change when comparing different views of the same anatomy, or even slightly different views in the same location, thus causing the optimal sound speed estimate to dither around. Through experimentation on actual datasets, an approach which seems to work well is to use a centroid calculation on a portion of the focus quality values that exceed a specified fraction of the focus quality contrast range, i.e., greater than 25%, after interpolating onto a higher density sound speed grid $c_m$. The centroid calculation helps reduce the dependence on the focus quality peak moving around; using the upper portion of the focus quality helps ensure that long tails in $Q_{f\_dB}(c)$ do not overly bias the centroid calculation. This is given by $$c_{body}^{opt} = \frac{\sum_{m \in m_\geq} c_m Q_{fTi\_dB}(c_m)}{\sum_{m \in m_\geq} Q_{fTi\_dB}(c_m)}$$

$$m_\geq : Q_{fTi\_dB}(c_{m_\geq}) \geq \max[Q_{fTi\_dB}(c_m)] + \Delta Q_{fThreshold\_dB}$$

$$Q_{fTi\_dB}(c_m) = \text{spline\_interpolate}[Q_{fT\_dB}(c_n), c_m]$$

where $\Delta Q_{fThreshold\_dB}$ is set to a suitable value such as −1 dB, etc.

Block 409 generates the receive reference delay profiles using the estimated body sound speed. Block 410 saves the receive delay profiles. Block 411 involves re-running the STC algorithm to produce new timing parameters, generating the reconstruction look-up table $LUT_R$, updating any GUI parameters needed, and finally, returning the user to live imaging.

There are other ways in which to compute the focus quality parameters. For example, averaging over normalized spatial frequency may be performed prior to averaging over range, producing a range dependent focus quality function $Q_f(r,c)$. The computation of the focus quality parameters $Q_{f\_dB}(c)$, etc., can be performed using a weighted average over range, where the weighting can be based upon the deviation the peak (or other appropriate calculation) varies from the mean peak, or based upon other parameters computed from the data.

There are other uses for the focus quality parameters. For example, the range variation in the focus quality $Q_f(r,c)$ can potentially be used to infer the depth dependence of sound speed. Another example is potentially using the focus quality variation with sound speed to determine the sound speed homogeneity of the body and alter imaging parameters to improve the image under these conditions, such as changing frequency, etc.

It is to be understood that the above description is intended to be illustrative and not restrictive. Many embodiments will be apparent to those of skill in the art upon reviewing the above description. The scope of the invention should, therefore, be determined not with reference to the above description, but instead should be determined with reference to the appended claims along with their full scope of equivalents.

What is claimed is:

1. A method of processing data for generating an ultrasound image, the method comprising the steps, carried out during an ultrasound examination, of:
   obtaining a set of channel data by digitizing ultrasound image data produced by an ultrasound scanner in performing an image scan;
   storing the set of channel data in a computer-readable storage medium, the set of stored channel data representing at least a selected image region of a frame of channel data;
   for the set of stored channel data,
      reconstructing a plurality of ultrasound images corresponding to a plurality of trial values of at least one parameter to be optimized using the same set of stored channel data in the computer-readable storage medium for each of the plurality of trial values;
      evaluating an image quality of the reconstructed ultrasound image for each trial value of the at least one parameter including computing one or more image focus quality parameters wherein computing one or more image focus quality parameters comprises providing a focus quality spectrum of the reconstructed ultrasound image based on the reconstructed ultrasound image for that trial value;
      determining the optimized value of the at least one parameter based on the evaluated image quality including determining the optimal value of the at least one parameter to be optimized by comparing the one or more image focus quality parameters; and
   using the optimized value in connection with processing of additional channel data.

2. The method of claim 1 wherein evaluating the image quality comprises computing a figure of merit for the reconstructed ultrasound image for each trial value of the at least one parameter.

3. The method of claim 1 further comprising performing actual imaging using the optimized value of the at least one parameter to produce an image frame.

4. The method of claim 1 wherein the obtaining, storing, reconstructing, evaluating, and determining are performed in real time.

5. The method of claim 1 wherein the at least one parameter includes one or more of:
   a sound speed through an object being scanned, the sound speed being used to process the channel data to produce an image frame from the image scan;
   transmit control parameters for a transmitter of the ultrasound scanner to specify at least one of transmit waveform, aperture function, delay profile, and pulsed repetition frequency for one or more imaging modes;
   electronic array focusing parameters for a receiver of the ultrasound scanner to specify at least one of front end filter, front end gain, and receive aperture function as a function of time/depth and the time delay profiles for image reconstruction; or
   image processing parameters for an image data processor of the ultrasound scanner to specify at least one of display dynamic range, gray or color maps, and spatial/temporal filtering.

6. The method of claim 1 wherein:
   evaluating the image quality comprises selecting an image region for evaluation; and
   the one or more image focus quality parameters are used to maximize an overall lateral spatial resolution of the selected image region due to improved focusing.

7. The method of claim 1 wherein the focus quality spectrum $Q_f(s,c)$ is selected from one of:

$$\text{Square of Sums} - Q_f(s, c) = \left[ \frac{1}{N_r} \sum_{r=r_1(c)}^{r=r_2(c)} |FFT\{|z_{IQ}(r, usl, c)|^2\}| \right]^2 ; \quad (a)$$

$$\text{Sum of Squares} - Q_f(s, c) = \frac{1}{N_r} \sum_{r=r_1(c)}^{r=r_2(c)} |FFT\{|z_{IQ}(r, usl, c)|^2\}|^2; \quad (b)$$

or $$Q_f(s, c) = \frac{1}{N_r} \sum_{r=r_1(c)}^{r=r_2(c)} |FFT\{z_{IQ}(r, usl, c)\}|^2 \text{ or} \quad (c)$$

$$\frac{1}{N_r} \left[ \sum_{r=r_1(c)}^{r=r_2(c)} |FFT\{z_{IQ}(r, usl, c)\}| \right]^2$$

where $z_{IQ}$ is a reconstructed in-phase/quadrature (I/Q) image region, $N_r$ is the number of range samples averaged from starting range $r_1(c)$ to ending range $r_2(c)$—both a function of the trial sound speed c, and where FFT{•} indicates a lateral spatial transform across usl (ultrasound line), and s is a normalized spatial frequency.

8. The method of claim 1 wherein the at least one parameter comprises a sound speed through an object being scanned, the sound speed being used to process the channel data to produce an image frame from the image scan, the image frame having an image scaling; further comprising:
altering transmit and/or receive focusing of the image scan based upon an optimized sound speed, while maintaining the image scaling of the image frame in spite of a change in the sound speed.

9. The method of claim 1 further comprising the step, performed after storing the channel data, of ceasing obtaining channel data while reconstructing the plurality of ultrasound images, evaluating the image quality of each of the reconstructed ultrasound images, and determining the optimized value of the at least one parameter.

10. A method of processing data for generating an ultrasound image, the method comprising the steps, carried out during an ultrasound examination, of:
obtaining multiple sets of channel data by digitizing ultrasound image data produced by an ultrasound scanner in performing an image scan;
storing the multiple sets of channel data in a computer-readable storage medium, each set of stored channel data representing at least a selected image region of a respective frame of channel data;
for each particular set of stored channel data,
reconstructing a plurality of ultrasound images corresponding to a plurality of trial values of at least one parameter to be optimized using that same particular set of stored channel data in the computer-readable storage medium for each of the plurality of trial values;
for each of the plurality of reconstructed ultrasound images based on that particular set of stored channel data, evaluating an image quality of that reconstructed ultrasound image by computing a figure of merit for that reconstructed ultrasound image;
determining the optimized value of the at least one parameter by combining the figures of merit for the multiple sets of channel data to provide combined figures of merit; and
using the optimized value in connection with further processing of additional channel data.

11. The method of claim 10 wherein obtaining channel data by digitizing ultrasound image data is ceased while ultrasound images are reconstructed, image qualities are evaluated, and the optimized value of the at least one parameter is determined.

12. An ultrasound system comprising:
a channel data memory to store a set of channel data obtained by digitizing ultrasound image data produced by an image scan;
an image data processor configured to process, for a set of stored channel data representing at least a selected image region of a particular frame of channel data, the same set of stored channel data in the memory to reconstruct a plurality of ultrasound images corresponding to a plurality of trial values of at least one parameter to be optimized; and
a parameter optimization unit configured to
compute one or more image focus quality parameters in order to evaluate an image quality for each of the plurality of reconstructed ultrasound images corresponding to the plurality of trial values of the at least one parameter, wherein the parameter optimization unit is configured to provide a focus quality spectrum of the image for use in computing the one or more image focus quality parameters,
determine the optimized value of the at least one parameter based on the evaluated image quality by comparing the one or more image focus quality parameters, and
provide the optimized value for use in connection with processing of additional channel data.

13. The ultrasound system of claim 12 wherein the parameter optimization unit is configured to evaluate the image quality by computing a figure of merit for the reconstructed ultrasound image for each trial value of the at least one parameter.

14. The ultrasound system of claim 12 wherein the image data processor is configured to perform actual imaging using the optimized value of the at least one parameter to produce an image frame, and further comprising a display to display the produced image frame.

15. The ultrasound system of claim 12 wherein the at least one parameter includes one or more of:
a sound speed through an object being scanned, the sound speed being used to process the channel data to produce an image frame from the image scan;
transmit control parameters for a transmitter of the ultrasound scanner to specify at least one of transmit waveform, aperture function, delay profile, and pulsed repetition frequency for one or more imaging modes;
electronic array focusing parameters for a receiver of the ultrasound scanner to specify at least one of front end filter, front end gain, and receive aperture function as a function of time/depth and the time delay profiles for image reconstruction; or
image processing parameters for an image data processor of the ultrasound scanner to specify at least one of display dynamic range, gray or color maps, and spatial/temporal filtering.

16. The ultrasound system of claim 12 wherein:
the parameter optimization unit is configured to select an image region for evaluation; and
the one or more image focus quality parameters are used to maximize an overall lateral spatial resolution of the selected image region due to improved focusing.

17. The ultrasound system of claim 12 wherein the focus quality spectrum $Q_f(s,c)$ is selected from one of:

$$\text{Square of Sums} - Q_f(s, c) = \left[\frac{1}{N_r}\sum_{r=r_1(c)}^{r=r_2(c)} |FFT\{|z_{IQ}(r, usl, c)|^2\}|\right]^2; \quad (a)$$

$$\text{Sum of Squares} - Q_f(s, c) = \frac{1}{N_r}\sum_{r=r_1(c)}^{r=r_2(c)} |FFT\{|z_{IQ}(r, usl, c)|^2\}|^2; \quad (b)$$

or $$Q_f(s, c) = \frac{1}{N_r}\sum_{r=r_1(c)}^{r=r_2(c)} |FFT\{z_{IQ}(r, usl, c)\}|^2 \text{ or} \quad (c)$$

$$\frac{1}{N_r}\left[\sum_{r=r_1(c)}^{r=r_2(c)} |FFT\{z_{IQ}(r, usl, c)\}|\right]^2$$

where $z_{IQ}$ is a reconstructed in-phase/quadrature (I/Q) image region, $N_r$ is the number of range samples averaged from starting range $r_1(c)$ to ending range $r_2(c)$—both a function of the trial sound speed c, and where FFT{•} indicates a lateral spatial transform across usl (ultrasound line), and s is a normalized spatial frequency.

18. The ultrasound system of claim 12 wherein:
the parameter optimization unit is configured to evaluate the image quality by computing a figure of merit for the reconstructed ultrasound image for each trial value of the at least one parameter;
multiple sets of channel data are stored by the channel data memory, and processed by the image data processor and the parameter optimization unit; and
the parameter optimization unit is configured to combine the figure of merits for the multiple sets of channel data to provide a combined figure of merit.

19. The ultrasound system of claim 12 wherein obtaining channel data by digitizing ultrasound image data is ceased while the image data processor processes the stored channel data and the parameter optimization unit computes the one or more image focus quality parameters and determines the optimized value of the at least one parameter.

20. An ultrasound system comprising:
a channel data memory to store multiple sets of channel data obtained by digitizing ultrasound image data produced by an image scan, each set of stored channel data representing at least a selected image region of a respective particular frame of channel data;
an image data processor configured to process each set of stored channel data in the memory to reconstruct for that set of stored channel data a plurality of ultrasound images corresponding to a plurality of trial values of at least one parameter to be optimized; and
a parameter optimization unit including a parameter optimization program stored in a computer readable storage medium;
wherein the parameter optimization program includes
code for evaluating, for each set of stored channel data, an image quality of each of the plurality of reconstructed ultrasound images corresponding to the plurality of trial values of the at least one parameter including code for computing, for each set of stored channel data, a figure of merit for each of the plurality of reconstructed ultrasound images corresponding to the plurality of trial values of the at least one parameter,
code for determining the optimized value of the at least one parameter based on the evaluated image quality including code for combining the figures of merit for the multiple sets of channel data to provide combined figures of merit, and
code for providing the optimized value for use in connection with processing of additional channel data.

21. The ultrasound system of claim 20 wherein code for evaluating the image quality comprises code for computing a figure of merit for the reconstructed ultrasound image for each trial value of the at least one parameter.

22. The ultrasound system of claim 20 wherein the at least one parameter includes one or more of:
a sound speed through an object being scanned, the sound speed being used to process the channel data to produce an image frame from the image scan;
transmit control parameters for a transmitter of the ultrasound scanner to specify at least one of transmit waveform, aperture function, delay profile, and pulsed repetition frequency for one or more imaging modes;
electronic array focusing parameters for a receiver of the ultrasound scanner to specify at least one of front end filter, front end gain, and receive aperture function as a function of time/depth and the time delay profiles for image reconstruction; or
image processing parameters for an image data processor of the ultrasound scanner to specify at least one of display dynamic range, gray or color maps, and spatial/temporal filtering.

23. The ultrasound system of claim 20 wherein the parameter optimization program further includes code for selecting an image region for evaluation.

24. The ultrasound system of claim 23 wherein:
the code for evaluating the image quality comprises code for computing one or more image focus quality parameters; and
the code for determining the optimized value comprises code for determining the optimal value of the at least one parameter to be optimized by comparing the one or more image focus quality parameters.

25. The ultrasound system of claim 24 wherein the one or more image focus quality parameters are used to maximize an overall lateral spatial resolution of the selected image region due to improved focusing.

26. The ultrasound system of claim 20 wherein obtaining channel data by digitizing ultrasound image data is ceased while ultrasound images are reconstructed, image qualities are evaluated, and the optimized value of the at least one parameter is determined.

27. An ultrasound system comprising:
a channel data memory to store multiple sets of channel data obtained by digitizing ultrasound image data produced by an image scan, each set of stored channel data representing at least a selected image region of a respective frame of channel data;
means for processing the multiple sets of stored channel data in the memory to reconstruct, for each set of stored channel data, a plurality of ultrasound images corresponding to a plurality of trial values of at least one parameter to be optimized;

means for evaluating, for each set of stored channel data, an image quality of each of the plurality of reconstructed ultrasound images corresponding to the plurality of trial values of the at least one parameter including means for computing a figure of merit for each of the plurality of reconstructed ultrasound images corresponding to the plurality of trial values of the at least one parameter;

means for determining the optimized value of the at least one parameter based on the evaluated image quality including means for combining the figures of merit for the multiple sets of channel data to provide combined figures of merit; and means for providing the optimized value for use in connection with processing of additional channel data.

28. The ultrasound system of claim 27 wherein the at least one parameter includes one or more of:

a sound speed through an object being scanned, the sound speed being used to process the channel data to produce an image frame from the image scan;

transmit control parameters for a transmitter of the ultrasound scanner to specify at least one of transmit waveform, aperture function, delay profile, and pulsed repetition frequency for one or more imaging modes;

electronic array focusing parameters for a receiver of the ultrasound scanner to specify at least one of front end filter, front end gain, and receive aperture function as a function of time/depth and the time delay profiles for image reconstruction; or image processing parameters for an image data processor of the ultrasound scanner to specify at least one of display dynamic range, gray or color maps, and spatial/temporal filtering.

29. The ultrasound system of claim 27 wherein the image quality is represented by one or more image focus quality parameters are used to maximize an overall lateral spatial resolution of the selected image region due to improved focusing.

30. The ultrasound system of claim 27 wherein obtaining channel data by digitizing ultrasound image data is ceased while ultrasound images are reconstructed, image qualities are evaluated, and the optimized value of the at least one parameter is determined.

31. An ultrasound system comprising:

a channel data memory configured to store a set of channel data obtained by digitizing ultrasound image data produced by an image scan, the set of stored channel data representing at least a selected image region of a frame of channel data;

means for processing the set of stored channel data in the memory to reconstruct a plurality of ultrasound images corresponding to a plurality of trial values of at least one parameter to be optimized; and means for evaluating an image quality of each of the plurality of reconstructed ultrasound images corresponding to the plurality of trial values of the at least one parameter including means for computing a figure of merit for each of the plurality of reconstructed ultrasound images corresponding to the plurality of trial values of the at least one parameter;

means for determining the optimal value of the at least one parameter by comparing the figures of merit for the plurality of reconstructed ultrasound images; and means for providing the optimized value for use in connection with processing of additional channel data.

* * * * *